United States Patent
Ludwig et al.

(10) Patent No.: US 10,214,586 B2
(45) Date of Patent: Feb. 26, 2019

(54) PD-L1 ANTIBODIES

(71) Applicant: Eli Lilly and Company, Indianapolis, IN (US)

(72) Inventors: Dale Lincoln Ludwig, Denville, NJ (US); Marshall Davenport Snavely, Norwalk, CT (US); Yiwen Li, Woodcliff Lake, NJ (US); Juqun Shen, Flushing, NY (US); Vera Molkenthin, Tannesberg (DE)

(73) Assignee: Eli Lilly and Company, Indianapolis, IN (US)

( * ) Notice: Subject to any disclaimer, the term of this patent is extended or adjusted under 35 U.S.C. 154(b) by 314 days.

(21) Appl. No.: 15/239,959

(22) Filed: Aug. 18, 2016

(65) Prior Publication Data
US 2017/0058033 A1  Mar. 2, 2017

Related U.S. Application Data

(60) Provisional application No. 62/209,056, filed on Aug. 24, 2015.

(51) Int. Cl.
C07K 16/28 (2006.01)
A61K 39/395 (2006.01)
A61K 45/06 (2006.01)
A61K 39/00 (2006.01)

(52) U.S. Cl.
CPC ........ *C07K 16/2827* (2013.01); *A61K 39/395* (2013.01); *A61K 39/3955* (2013.01); *A61K 45/06* (2013.01); *C07K 16/2818* (2013.01); *A61K 2039/505* (2013.01); *C07K 2317/21* (2013.01); *C07K 2317/34* (2013.01); *C07K 2317/41* (2013.01); *C07K 2317/51* (2013.01); *C07K 2317/515* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 7,794,710 B2 | 9/2010 | Lieping et al. |
| 7,892,540 B2 | 2/2011 | Lieping et al. |
| 8,168,179 B2 | 5/2012 | Tasuku et al. |
| 8,617,546 B2 | 12/2013 | Chang et al. |
| 2010/0203056 A1 | 8/2010 | Irving et al. |
| 2013/0034559 A1 | 2/2013 | Queva et al. |

FOREIGN PATENT DOCUMENTS

| | | |
|---|---|---|
| WO | 200114556 A1 | 3/2001 |
| WO | 200139722 A2 | 6/2001 |
| WO | 2002078731 A1 | 10/2002 |
| WO | 2003042402 A2 | 5/2003 |
| WO | 2007005874 A2 | 1/2007 |
| WO | 2010027828 A2 | 3/2010 |
| WO | 2010036959 A2 | 4/2010 |
| WO | 2010077634 A1 | 7/2010 |
| WO | 2010098788 A2 | 9/2010 |
| WO | 2011066389 A1 | 6/2011 |
| WO | 2012145493 A1 | 10/2012 |
| WO | 2013079174 A1 | 6/2013 |
| WO | 2013181452 A1 | 12/2013 |
| WO | 2013181634 A2 | 12/2013 |
| WO | 2014022758 A1 | 2/2014 |
| WO | 2014055897 A2 | 4/2014 |
| WO | 2014100079 A1 | 6/2014 |
| WO | 2016007235 A1 | 1/2016 |

OTHER PUBLICATIONS

Herbst, et al., "Predictive correlates of response to the anti-PD-L1 antibody MPDL3280A in cancer patients," Nature; 515(7528), pp. 515: 563 (2014).
Cha, et al., "PD-L1 Inhibition With MPDL3280A for Solid Tumors," Seminars in Oncology; 42(3), pp. 484-487 (Jun. 2015).
Ibrahim, et al., "PD-L1 Blockade for Cancer Treatment: MEDI4736," Seminars in Oncology; 42(3), pp. 474-483 (Jun. 2015).
Dong, et al., "B7-H1, a third member of the B7 family, co-stimulates T-cell proliferation and interleukin-10 secretion," Nature Medicine; 5(12), pp. 1365-1369 (Dec. 1999).
Freeman, et al., "Engagement of the PD-1 Immunoinhibitory Receptor by a Novel B7 Family Member Leads to Negative Regulation of Lymphocyte Activation," J Exp, Med.; 192(7): 1027-1034 (2000).
Carter, et al., "PD-1:PD-L inhibitory pathway affects both CD4+ and CD8+ T cells and is overcome by IL-2," Eur J. Immunol; v32, pp. 634-643 (2002).
Dong, et al., "Tumor-associated B7-H1 promotes T-cell apoptosis: A potential mechanism of immune evasion," Nature Medicine; 8(8), pp. 793-800 (Aug. 2002).
Latchman, et al., "PD-L2 is a second ligand for PD-1 and inhibits T cell activation," Nature Immunology; 2(3), pp. 261-268 (2001).

*Primary Examiner* — Ilia I Ouspenski
(74) *Attorney, Agent, or Firm* — Robert Brian Johnson; Margaret M. Tomaska

(57) ABSTRACT

The present invention relates to antibodies that bind human programmed cell death 1 ligand 1 (PD-L1), and may be useful for treating solid and hematological tumors alone and in combination with chemotherapy and other cancer therapeutics.

13 Claims, No Drawings
Specification includes a Sequence Listing.

SEQUENCE LISTING

<160> NUMBER OF SEQ ID NOS: 13

<210> SEQ ID NO 1
<211> LENGTH: 290
<212> TYPE: PRT
<213> ORGANISM: Artificial Sequence
<220> FEATURE:
<223> OTHER INFORMATION: Synthetic construct

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

```
Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
            275                 280                 285

Glu Thr
    290

<210> SEQ ID NO 2
<211> LENGTH: 13
<212> TYPE: PRT
<213> ORGANISM: Artificial Sequence
<220> FEATURE:
<223> OTHER INFORMATION: Synthetic construct

<400> SEQUENCE: 2

Lys Ala Ser Gly Gly Thr Phe Ser Ser Tyr Ala Ile Ser
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic construct

<400> SEQUENCE: 3

Gly Ile Ile Pro Ile Phe Gly Thr Ala Asn Tyr Ala Gln Lys Phe Gln
1               5                   10                  15

Gly

<210> SEQ ID NO 4
<211> LENGTH: 16
<212> TYPE: PRT
<213> ORGANISM: Artificial Sequence
<220> FEATURE:
<223> OTHER INFORMATION: Synthetic construct

<400> SEQUENCE: 4

Ala Arg Ser Pro Asp Tyr Ser Pro Tyr Tyr Tyr Tyr Gly Met Asp Val
```

<210> SEQ ID NO 5
<211> LENGTH: 13
<212> TYPE: PRT
<213> ORGANISM: Artificial Sequence
<220> FEATURE:
<223> OTHER INFORMATION: Synthetic construct

<400> SEQUENCE: 5

Ser Gly Ser Ser Ser Asn Ile Gly Ser Asn Thr Val Asn
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Synthetic construct

<400> SEQUENCE: 6

Tyr Gly Asn Ser Asn Arg Pro Ser
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic construct

<400> SEQUENCE: 7

Gln Ser Tyr Asp Ser Ser Leu Ser Gly Ser Val
1               5                   10

<210> SEQ ID NO 8
<211> LENGTH: 123
<212> TYPE: PRT
<213> ORGANISM: Artificial Sequence
<220> FEATURE:
<223> OTHER INFORMATION: Synthetic construct

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Asp Tyr Ser Pro Tyr Tyr Tyr Gly Met Asp Val
            100                 105                 110

Trp Gly Gln Gly Thr Thr Val Thr Val Ser Ser
        115                 120

<210> SEQ ID NO 9
<211> LENGTH: 111
<212> TYPE: PRT

```
<213> ORGANISM: Artificial Sequence
<220> FEATURE:
<223> OTHER INFORMATION: Synthetic construct

<400> SEQUENCE: 9

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Gly Asn Ser Asn Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Ile Lys Leu Thr Val Leu Gly
                100                 105                 110

<210> SEQ ID NO 10
<211> LENGTH: 453
<212> TYPE: PRT
<213> ORGANISM: Artificial Sequence
<220> FEATURE:
<223> OTHER INFORMATION: Synthetic construct

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Asp Tyr Ser Pro Tyr Tyr Tyr Gly Met Asp Val
                100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220
```

```
Ser Cys Asp Lys Thr His Thr Cys Pro Pro Cys Pro Ala Pro Glu Ala
225                 230                 235                 240

Glu Gly Ala Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 11
<211> LENGTH: 216
<212> TYPE: PRT
<213> ORGANISM: Artificial Sequence
<220> FEATURE:
<223> OTHER INFORMATION: Synthetic construct

<400> SEQUENCE: 11

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Gly Asn Ser Asn Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Ile Lys Leu Thr Val Leu Gly Gln
            100                 105                 110

Pro Lys Ala Ala Pro Ser Val Thr Leu Phe Pro Pro Ser Ser Glu Glu
            115                 120                 125
```

```
Leu Gln Ala Asn Lys Ala Thr Leu Val Cys Leu Ile Ser Asp Phe Tyr
    130                 135                 140
Pro Gly Ala Val Thr Val Ala Trp Lys Ala Asp Ser Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
                180                 185                 190
Arg Ser Tyr Ser Cys Gln Val Thr His Glu Gly Ser Thr Val Glu Lys
            195                 200                 205
Thr Val Ala Pro Ala Glu Cys Ser
    210                 215

<210> SEQ ID NO 12
<211> LENGTH: 1359
<212> TYPE: DNA
<213> ORGANISM: Artificial Sequence
<220> FEATURE:
<223> OTHER INFORMATION: Synthetic construct

<400> SEQUENCE: 12
```

| | | | | | |
|---|---|---|---|---|---|
| caggtccagc | tggtccagtc | aggggccgag | gtcaaaaagc | cagggtcatc | tgtcaaagtg | 60 |
| tcttgtaagg | catccggggg | cacattttcc | agctacgcta | tctcctgggt | gagacaggca | 120 |
| ccagggcagg | gtctggagtg | gatgggcgga | atcattccca | tcttcgggac | cgccaactac | 180 |
| gctcagaagt | tcagggaag | ggtcactatt | accgccgaca | aaagcacatc | tactgcttat | 240 |
| atggagctgt | ctagtctgag | gtctgaagat | accgcagtgt | actattgcgc | ccggagtccc | 300 |
| gactatagcc | cttactatta | ctatggcatg | gatgtctggg | gccagggaac | cacagtgaca | 360 |
| gtctcatccg | ctagcaccaa | gggcccatcg | gtcttccccc | tggcaccctc | ctccaagagc | 420 |
| acctctgggg | gcacagcggc | cctgggctgc | ctggtcaagg | actacttccc | cgaaccggtg | 480 |
| acggtgtcgt | ggaactcagg | cgccctgacc | agcggcgtgc | acaccttccc | ggctgtccta | 540 |
| cagtcctcag | gactctactc | cctcagcagc | gtggtgaccg | tgccctccag | cagcttgggc | 600 |
| acccagacct | acatctgcaa | cgtgaatcac | aagcccagca | acaccaaggt | ggacaagaga | 660 |
| gttgagccca | atcttgtgac | aaaactcac | acatgcccac | cgtgcccagc | acctgaagcc | 720 |
| gagggggcac | cgtcagtctt | cctcttcccc | ccaaaaccca | aggacaccct | catgatctcc | 780 |
| cggacccctg | aggtcacatg | cgtggtggtg | gacgtgagcc | acgaagaccc | tgaggtcaag | 840 |
| ttcaactggt | atgtggacgg | cgtggaggtg | cataatgcca | agacaaagcc | gcgggaggag | 900 |
| cagtacaaca | gcacgtaccg | tgtggtcagc | gtcctcaccg | tcctgcacca | agactggctg | 960 |
| aatggcaagg | agtacaagtg | caaggtctcc | aacaaagccc | tcccatcctc | catcgagaaa | 1020 |
| accatctcca | aagccaaagg | gcagccccga | gaaccacagg | tgtacaccct | gcccccatcc | 1080 |
| cgggaggaga | tgaccaagaa | ccaagtcagc | ctgacctgcc | tggtcaaagg | cttctatccc | 1140 |
| agcgacatcg | ccgtggagtg | ggagagcaat | gggcagccgg | agaacaacta | caagaccacg | 1200 |
| cctcccgtgc | tggactccga | cggctccttc | ttcctctatt | ccaagctcac | cgtggacaag | 1260 |
| agcaggtggc | agcaggggaa | cgtcttctca | tgctccgtga | tgcatgaggc | tctgcacaac | 1320 |
| cactacacgc | agaagagcct | ctccctgtct | ccgggcaaa | | | 1359 |

<210> SEQ ID NO 13
<211> LENGTH: 648
<212> TYPE: DNA
<213> ORGANISM: Artificial Sequence
<220> FEATURE:
<223> OTHER INFORMATION: Synthetic construct

<400> SEQUENCE: 13

```
cagtccgtcc tgacacagcc accctcagcc tctggcaccc ctgggcagcg agtgacaatc      60
tcttgttctg ggagttcctc aaatattggt agtaacaccg tgaattggta ccagcagctg     120
cccggcacag cacctaagct gctgatctat ggaaactcaa ataggccatc cggagtcccc     180
gaccggttct ctggtagtaa atcaggcact tccgccagcc tggctattag cgggctgcag     240
tctgaggacg aagccgatta ctattgccag tcttacgatt ccagcctgtc tggaagtgtg     300
tttggcggag ggatcaagct gaccgtcctg ggccagccta aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca caagtacgc ggccagcagc     540
tacctgagcc tgacgcctga gcagtggaag tcccacagaa gctacagctg ccaggtcacg     600
catgaaggga gcaccgtgga aagacagtg gcccctgcag aatgctct                   648
```

PD-L1 ANTIBODIES

The present invention relates to the field of medicine. More particularly, the present invention relates to antibodies that bind human programmed cell death 1 ligand 1 (PD-L1), and may be useful for treating solid and hematological tumors alone and in combination with chemotherapy and other cancer therapeutics.

Tumor cells escape detection and elimination by the immune system through multiple mechanisms. Immune checkpoint pathways are used in maintenance of self-tolerance and control of T cell activation, but cancer cells can use the pathways to suppress the anti-tumor response and prevent their destruction.

The PD-L1/human programmed cell death 1 (PD-1) pathway is one such immune checkpoint. Human PD-1 is found on T cells, and the binding of PD-L1 to PD-1 inhibits T cell proliferation and cytokine production. The PD-1/PD-L1 inhibitory axis has been subjugated by tumors as part of the natural selective process that shapes tumor evolution in the context of an anti-tumor immune response. PD-L1 also binds B7-1 (CD80); B7-1 is another negative regulator of T cell activation. Accordingly, PD-L1 is aberrantly expressed by a variety of tumor types, and increased expression of PD-L1 on tumor cells has been found to be correlated with a worse prognosis in many cancers. PD-L1 expression is also up-regulated in the tumor microenvironment in immune and other cells as a result of immune activation and production of pro-inflammatory cytokines, further contributing to the establishment of a T-cell immunosuppressive milieu. Blocking PD-L1 may facilitate the re-activation of tumor-reacting T cells, restoring their ability to effectively detect and kill tumor cells.

A human IgG1 antibody against human PD-L1, MPDL3280A, has been shown to block binding to PD-1 and B7-1, and has been tested in human clinical trials (Herbst et al., Nature (2014) 515:563; Cha et al., Seminars in Oncology (2015) 42(3):484; and U.S. patent application 2010/0203056). A human IgG1 antibody against human PD-L1, MEDI4736, has been shown to block binding to PD-1 and B7-1, and has been tested in human clinical trials (Ibrahim et al., Seminars in Oncology (2015) 42(3):474; and U.S. patent application 2013/0034559).

There remains a need to provide alternative antibodies that bind human PD-L1 and neutralize the PD-L1 interactions with PD-1 and B7-1. In particular, there remains a need to provide PD-L1 antibodies that bind with more favorable attributes, such as better association rates. Faster association to the target can translate into better in vivo activity for a therapeutic antibody. Also, there remains a need to provide PD-L1 antibodies that better enhance the T cell response to a tumor, as measured by influence on tumor size, by the level of infiltration of CD3-positive T cells, and by the percentage of T cells that are CD8-positive in in vivo models.

Certain antibodies of the present invention mediate enhanced T cell response to a tumor as measured by tumor size compared to certain prior art antibodies in established and non-established tumor models. Certain antibodies of the present invention mediate enhanced T cell response to a tumor as measured by CD3-positive T cell infiltration compared to certain prior art antibodies in a model.

Accordingly, in some embodiments the present invention provides an antibody that binds human PD-L1 (SEQ ID NO: 1), comprising a light chain (LC) and a heavy chain (HC), wherein the light chain comprises a light chain variable region (LCVR) and the heavy chain comprises a heavy chain variable region (HCVR), and wherein the LCVR comprises light chain complementarity determining regions LCDR1, LCDR2, and LCDR3 consisting of the amino acid sequences SGSSSNIGSNTVN (SEQ ID NO: 5), YGNSNRPS (SEQ ID NO: 6), and QSYDSSLSGSV (SEQ ID NO: 7), respectively, and wherein the HCVR comprises heavy chain complementarity determining regions HCDR1, HCDR2, and HCDR3 consisting of the amino acid sequences KASGGTFSSYAIS (SEQ ID NO: 2), GIIPIFGTANYAQKFQG (SEQ ID NO: 3), and ARSPDYSPYYYYGMDV (SEQ ID NO: 4), respectively.

In some embodiments, the present invention provides an antibody, comprising a light chain (LC) and a heavy chain (HC), wherein the light chain comprises a light chain variable region (LCVR) and the heavy chain comprises a heavy chain variable region (HCVR), wherein the LCVR has the amino acid sequence given in SEQ ID NO: 9, and the HCVR has the amino acid sequence given in SEQ ID NO: 8.

In some embodiments, the present invention provides an antibody, wherein the LC has the amino acid sequence given in SEQ ID NO: 11, and the HC has the amino acid sequence given in SEQ ID NO: 10.

In an embodiment, the present invention provides an antibody, comprising two light chains and two heavy chains, wherein each light chain has the amino acid sequence given in SEQ ID NO: 11, and each heavy chain has the amino acid sequence given in SEQ ID NO: 10.

In a further embodiment, the present invention provides an antibody, wherein one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain.

In a further embodiment, the present invention provides an antibody, wherein the antibody is glycosylated.

In an embodiment, the present invention provides a mammalian cell, comprising a DNA molecule comprising a polynucleotide sequence encoding a polypeptide having an amino acid sequence of SEQ ID NO: 11 and a polynucleotide sequence encoding a polypeptide having an amino acid sequence of SEQ ID NO: 10, wherein the cell is capable of expressing an antibody comprising a light chain having an amino acid sequence of SEQ ID NO: 11 and a heavy chain having an amino acid sequence of SEQ ID NO: 10.

In a further embodiment, the present invention provides a process for producing an antibody, comprising a light chain having an amino acid sequence of SEQ ID NO: 11 and a heavy chain having an amino acid sequence of SEQ ID NO: 10, comprising cultivating a mammalian cell of the present invention under conditions such that the antibody is expressed, and recovering the expressed antibody.

In a further embodiment, the present invention provides an antibody produced by a process of the present invention.

In an embodiment, the present invention provides a pharmaceutical composition, comprising an antibody of the present invention, and an acceptable carrier, diluent, or excipient.

In an embodiment, the present invention provides a method of treating cancer, comprising administering to a patient in need thereof, an effective amount of an antibody of the present invention. In a further embodiment, the present invention provides a method of treating cancer, comprising administering to a patient in need thereof, an effective amount of an antibody of the present invention, wherein the cancer is melanoma, lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or hepatocellular carcinoma.

In a further embodiment, the present invention provides a method of treating cancer, wherein the cancer is melanoma. In a further embodiment, the present invention provides a method of treating cancer, wherein the cancer is lung cancer. In a further embodiment, the present invention provides a method of treating cancer, wherein the cancer is head and neck cancer. In a further embodiment, the present invention provides a method of treating cancer, wherein the cancer is colorectal cancer. In a further embodiment, the present invention provides a method of treating cancer, wherein the cancer is pancreatic cancer. In a further embodiment, the present invention provides a method of treating cancer, wherein the cancer is gastric cancer. In a further embodiment, the present invention provides a method of treating cancer, wherein the cancer is kidney cancer. In a further embodiment, the present invention provides a method of treating cancer, wherein the cancer is bladder cancer. In a further embodiment, the present invention provides a method of treating cancer, wherein the cancer is prostate cancer. In a further embodiment, the present invention provides a method of treating cancer, wherein the cancer is breast cancer. In a further embodiment, the present invention provides a method of treating cancer, wherein the cancer is ovarian cancer. In a further embodiment, the present invention provides a method of treating cancer, wherein the cancer is esophageal cancer. In a further embodiment, the present invention provides a method of treating cancer, wherein the cancer is soft tissue sarcoma. In a further embodiment, the present invention provides a method of treating cancer, wherein the cancer is hepatocellular carcinoma.

In a further embodiment, these methods comprise the administration of an effective amount of the antibody of the present invention in simultaneous, separate, or sequential combination with one or more anti-tumor agents. Non-limiting examples of anti-tumor agents include ramucirumab, necitumumab, olaratumab, galunisertib, abemaciclib, cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), and cetuximab.

In a further embodiment, these methods comprise the administration of an effective amount of the compound of the present invention in simultaneous, separate, or sequential combination with one or more immuno-oncology agents. Non-limiting examples of immuno-oncology agents include nivolumab, ipilimumab, pidilizumab, pembrolizumab, tremelimumab, urelumab, lirilumab, atezolizumab, and durvalumab.

In an embodiment, the present invention provides an antibody of the present invention, for use in therapy. In an embodiment, the present invention provides an antibody of the present invention, for use in the treatment of cancer. In a further embodiment, the present invention provides an antibody of the present invention, for use in the treatment of cancer, wherein the cancer is melanoma, lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or hepatocellular carcinoma.

In a further embodiment, the present invention provides an antibody of the present invention, for use in the treatment of cancer, wherein the cancer is melanoma. In a further embodiment, the present invention provides an antibody of the present invention, for use in the treatment of cancer, wherein the cancer is lung cancer. In a further embodiment, the present invention provides an antibody of the present invention, for use in the treatment of cancer, wherein the cancer is head and neck cancer. In a further embodiment, the present invention provides an antibody of the present invention, for use in the treatment of cancer, wherein the cancer is colorectal cancer. In a further embodiment, the present invention provides an antibody of the present invention, for use in the treatment of cancer, wherein the cancer is pancreatic cancer. In a further embodiment, the present invention provides an antibody of the present invention, for use in the treatment of cancer, wherein the cancer is gastric cancer. In a further embodiment, the present invention provides an antibody of the present invention, for use in the treatment of cancer, wherein the cancer is kidney cancer. In a further embodiment, the present invention provides an antibody of the present invention, for use in the treatment of cancer, wherein the cancer is bladder cancer. In a further embodiment, the present invention provides an antibody of the present invention, for use in the treatment of cancer, wherein the cancer is prostate cancer. In a further embodiment, the present invention provides an antibody of the present invention, for use in the treatment of cancer, wherein the cancer is breast cancer. In a further embodiment, the present invention provides an antibody of the present invention, for use in the treatment of cancer, wherein the cancer is ovarian cancer. In a further embodiment, the present invention provides an antibody of the present invention, for use in the treatment of cancer, wherein the cancer is esophageal cancer. In a further embodiment, the present invention provides an antibody of the present invention, for use in the treatment of cancer, wherein the cancer is soft tissue sarcoma. In a further embodiment, the present invention provides an antibody of the present invention, for use in the treatment of cancer, wherein the cancer is hepatocellular carcinoma.

In a further embodiment, the present invention provides the antibody of the present invention for use in simultaneous, separate, or sequential combination with one or more anti-tumor agents. In a further embodiment, the present invention provides the antibody of the present invention for use in simultaneous, separate, or sequential combination with one or more anti-tumor agents selected from the group consisting of ramucirumab, necitumumab, olaratumab, galunisertib, abemaciclib, cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), and cetuximab, in the treatment of cancer.

In a further embodiment, the present invention provides the antibody of the present invention for use in simultaneous, separate, or sequential combination with one or more immuno-oncology agents. In a further embodiment, the present invention provides the antibody of the present invention for use in simultaneous, separate, or sequential combination with one or more immuno-oncology agents selected from the group consisting of nivolumab, ipilimumab, pidilizumab, pembrolizumab, tremelimumab, urelumab, lirilumab, atezolizumab, and durvalumab, in the treatment of cancer.

In a further embodiment, the present invention provides the use of an antibody of the present invention for the manufacture of a medicament for the treatment of cancer. In a further embodiment, the present invention provides the use of an antibody of the present invention for the manufacture of a medicament for the treatment of cancer, wherein the cancer is melanoma, lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or hepatocellular carcinoma.

In a further embodiment, the present invention provides the use of an antibody of the present invention in the manufacture of a medicament for the treatment of cancer wherein said medicament is to be administered simultaneously, separately, or sequentially with one or more anti-tumor agents. In a further embodiment, the present invention provides the use of an antibody of the present invention in the manufacture of a medicament for the treatment of cancer wherein said medicament is to be administered simultaneously, separately, or sequentially with one or more anti-tumor agents selected from the group consisting of ramucirumab, necitumumab, olaratumab, galunisertib, abemaciclib, cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), and cetuximab.

In a further embodiment, the present invention provides the use of an antibody of the present invention in the manufacture of a medicament for the treatment of cancer wherein said medicament is to be administered simultaneously, separately, or sequentially with one or more immuno-oncology agents. In a further embodiment, the present invention provides the use of an antibody of the present invention in the manufacture of a medicament for the treatment of cancer wherein said medicament is to be administered simultaneously, separately, or sequentially with one or more immuno-oncology agents selected from the group consisting of nivolumab, ipilimumab, pidilizumab, pembrolizumab, tremelimumab, urelumab, lirilumab, atezolizumab, and durvalumab, in the treatment of cancer.

An antibody of the present invention is an engineered, non-naturally occurring polypeptide complex. A DNA molecule of the present invention is a non-naturally occurring DNA molecule that comprises a polynucleotide sequence encoding a polypeptide having the amino acid sequence of one of the polypeptides in an antibody of the present invention.

The antibody of the present invention is an IgG type antibody and has "heavy" chains and "light" chains that are cross-linked via intra- and inter-chain disulfide bonds. Each heavy chain is comprised of an N-terminal HCVR and a heavy chain constant region ("HCCR"). Each light chain is comprised of a LCVR and a light chain constant region ("LCCR"). When expressed in certain biological systems, antibodies having native human Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

Optionally, certain antibodies of the present invention contain an Fc portion which is derived from human IgG$_1$. IgG1 is well known to bind to the proteins of the Fc-gamma receptor family (FcγR) as well as C1q. Interaction with these receptors can induce antibody-dependent cell cytotoxicity (ADCC) and complement-dependent cytotoxicity (CDC). Therefore, optionally, certain antibodies of the present invention are a fully human monoclonal antibody lacking Fc effector function (IgG1, lambda, Fc-null). To achieve an Fc-null IgG1 antibody, selective mutagenesis of residues is necessary within the CH2 region of its IgG1 Fc region Amino acid substitutions L234A, L235E, and G237A are introduced into IgG1 Fc to reduce binding to FcγRI, FcγRIIa, and FcγRIII, and substitutions A330S and P331S are introduced to reduce C1q-mediated complement fixation.

To reduce the potential induction of an immune response when dosed in humans, certain amino acids may require back-mutations to match antibody germline sequences. Certain antibodies of the present invention contain E1Q and S94R mutations in the variable heavy chain, and contain T76S and A80S mutations in the variable light chain.

The HCVR and LCVR regions can be further subdivided into regions of hyper-variability, termed complementarity determining regions ("CDRs"), interspersed with regions that are more conserved, termed framework regions ("FR"). Each HCVR and LCVR is composed of three CDRs and four 1-Rs, arranged from amino-terminus to carboxy-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues which form specific interactions with the antigen. There are currently three systems of CDR assignments for antibodies that are used for sequence delineation. The Kabat CDR definition (Kabat et al., "Sequences of Proteins of Immunological Interest," National Institutes of Health, Bethesda, Md. (1991)) is based upon antibody sequence variability. The Chothia CDR definition (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)) is based on three-dimensional structures of antibodies and topologies of the CDR loops. The Chothia CDR definitions are identical to the Kabat CDR definitions with the exception of HCDR1 and HCDR2. The North CDR definition (North et al., "A New Clustering of Antibody CDR Loop Conformations", Journal of Molecular Biology, 406, 228-256 (2011)) is based on affinity propagation clustering with a large number of crystal structures. For the purposes of the present invention, the North CDR definitions are used.

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region. Preferably for antibodies of the present invention, the light chain constant region is a lambda constant region.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibody of the present invention may readily be produced in mammalian cells such as CHO, NS0, HEK293 or COS cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host.

Various methods of protein purification may be employed and such methods are known in the art and described, for example, in Deutscher, *Methods in Enzymology* 182: 83-89 (1990) and Scopes, *Protein Purification: Principles and Practice,* 3rd Edition, Springer, N.Y. (1994).

In another embodiment of the present invention, the antibody, or the nucleic acids encoding the same, is provided in isolated form. As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80% (on a molar basis) of the macromolecular species present, preferably more than 90%, and more preferably more than 95%.

The antibody of the present invention, or pharmaceutical compositions comprising the same, may be administered by parenteral routes (e.g., subcutaneous and intravenous). An antibody of the present invention may be administered to a patient alone with pharmaceutically acceptable carriers, diluents, or excipients in single or multiple doses. Pharmaceutical compositions of the present invention can be prepared by methods well known in the art (e.g., *Remington: The Science and Practice of Pharmacy,* 22$^{nd}$ ed. (2012), A. Loyd et al., Pharmaceutical Press) and comprise an antibody, as disclosed herein, and one or more pharmaceutically acceptable carriers, diluents, or excipients.

The term "treating" (or "treat" or "treatment") refers to slowing, interrupting, arresting, alleviating, stopping, reducing, or reversing the progression or severity of an existing symptom, disorder, condition, or disease.

"Binds" as used herein in reference to the affinity of an antibody for human PD-L1 is intended to mean, unless indicated otherwise, a $K_D$ of less than about $1\times10^{-6}$ M, preferably, less than about $1\times10^{-9}$ M as determined by common methods known in the art, including by use of a surface plasmon resonance (SPR) biosensor at 37° C. essentially as described herein.

"Effective amount" means the amount of an antibody of the present invention or pharmaceutical composition comprising an antibody of the present invention that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects.

This invention is further illustrated by the following non-limiting example.

EXAMPLE 1: ANTIBODY EXPRESSION AND PURIFICATION

The polypeptides of the variable regions of the heavy chain and light chain, the complete heavy chain and light chain amino acid sequences of Antibody A, and the nucleotide sequences encoding the same, are listed below in the section entitled "Amino Acid and Nucleotide Sequences." In addition, the SEQ ID NOs for the light chain, heavy chain, light chain variable region, and heavy chain variable region of Antibody A are shown in Table 1.

The antibodies of the present invention, including, but not limited to, Antibody A can be made and purified essentially as follows. An appropriate host cell, such as HEK 293 or CHO, can be either transiently or stably transfected with an expression system for secreting antibodies using an optimal predetermined HC:LC vector ratio or a single vector system encoding both HC and LC. Clarified media, into which the antibody has been secreted, may be purified using any of many commonly-used techniques. For example, the medium may be conveniently applied to a MabSelect column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Antibody fractions may be detected, such as by SDS-PAGE, and then may be pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, multimodal, or hydroxyapatite chromatography. The purity of the antibody after these chromatography steps is greater than 95%. The product may be immediately frozen at −70° C. or may be lyophilized.

TABLE 1

| SEQ ID NOs | |
|---|---|
| | Antibody A |
| HCVR | 8 |
| LCVR | 9 |
| Heavy chain | 10 |
| Light chain | 11 |

Assays
In Vivo Activity—WINN Assay

The antibodies of the present invention can be tested for in vivo immunomodulatory activity with the Winn assay. In the Winn assay, human tumor cells and human immune cells (allogenic) are injected together at the same into an immunodeficient mouse, and then followed by dosing with an immunomodulatory agent. The ability of the immumomodulatory agent to delay or block tumor growth in the model can be assessed. Tumor volume is measured to determine the effect of the immunomodulatory agent in the assay and whether there is an enhancement of the immune response towards the tumor.

As used herein, 2.14H9OPT is a human IgG1 PD-L1 antibody that utilizes the heavy chain and light chain sequences from U.S. patent application 2013/0034559. As used herein, S70 is a human IgG1 PD-L1 antibody that utilizes the heavy chain and light chain sequences from U.S. patent application 2010/0203056. For both 2.14H9OPT and S70, the heavy chains were fused to the variable region of the human IgG1 constant region containing residue changes at L234A, L235E, G237A, A330S, and P331S, to silence effector functions related to Fc gamma receptors and complement cascade. For both 2.14H9OPT and S70, recombinant protein was expressed in mammalian cells and purified by standard ProA purification methods.

Enhancement of the immune response to allo-antigens by antibodies of the present invention may be tested in the NCI-H292 human NSCLC xenograft model. On day 0, NSG mice from Jackson Laboratories (7 weeks of age, female, in groups of 8-10 mice) are implanted into the flank subcutaneously with either $2\times10^6$ H292 cells, or a mixture of $2\times10^6$ H292 cells and $1\times10^6$ human PBMCs in HBSS (0.2 ml total volume). Starting on Day 1, mice are treated with an i.p. injection of antibody at 10 mg/kg, one time per week. Animal well-being and behavior, including grooming and ambulation are monitored at least twice per week.

Body weight and tumor volume are measured twice a week. Tumor specimens are collected on Day 36 from all groups. Immunohistochemical (IHC) staining is performed on tumor samples using rabbit anti-mouse CD3 antibody (cross-reactive with human, Abcam), followed by staining with a secondary HRP-conjugated anti-rabbit IgG (Dako).

Tumor volumes are measured twice per week starting on day 4 post cell implantation using electronic calipers. Tumor Volume (mm$^3$)=$\pi/6$*Length*Width$^2$. The antitumor efficacy is expressed as T/C ratio in percent and calculated as summarized below:

% T/C is calculated by the formula 100 $\Delta T/\Delta C$ if $\Delta T>0$ of the geometric mean values. $\Delta T$=mean tumor volume of the drug-treated group on the final day of the study–mean tumor volume of the drug-treated group on initial day of dosing; $\Delta C$=mean tumor volume of the control group on the final day of the study–mean tumor volume of the control group on initial day of dosing. Additionally, % Regression is calculated using the formula=100×$\Delta T/T_{initial}$ if $\Delta T<0$. Animals with no measurable tumors are considered as Complete Responders (CR) and tumors with >50% regressions were Partial Responders (PR).

Tumor volume data are analyzed through day 35 with a two-way repeated measures analysis of variance by time and treatment using the MIXED procedures in SAS software (Version 9.2). The response analyzed is the log transformation of tumor volume. The log transformation is necessary to equalize the variance across time and treatment groups. The correlation structure for the repeated measures model is Spatial Power. Predefined pairwise comparisons of treated group(s) to control group(s) for each time point are conducted.

Tumor sections from the model can also be analyzed for CD3-positive T cell infiltration by measuring the presence of CD3-positive T cells using staining for CD3 and analysis with the Aperio Scan scope. The IHC Nuclear Image Analysis macro detects nuclear staining for a target chromogen for the individual cells in those regions that are chosen by the user and quantifies their intensities. Three to five annotations are made from viable tumor area and used in adjusting the parameters until the algorithm results generate consistent cell identification. The macro is then saved and the slides logged in for analysis. The % CD3 positive cells as a percent of the total number of cells are calculated by the Aperio software.

Tumor Volume

In experiments performed essentially as described in this assay, Antibody A dosed at 10 mg/kg, qw, ip is well tolerated as monitored by body weight and clinical observations. When no immune cells are added to the immunodeficient animal as a control arm of the experiment (mice implanted with the lung cancer cell line H292, but with no PBMCs), treatment with Antibody A or 2.14H9OPT dosed at 10 mg/kg, qw, ip has no effect on H-292 tumor growth compared to treatment with human IgG.

When immune cells and the test antibody are added to the immunodeficient animal, Antibody A gives a significantly superior result to control IgG, while 2.14H9OPT does not. Mice co-implanted with NCI-H292 tumors and PBMCs and dosed with Antibody A at 10 mg/kg qw result in a T/C of 35% that is significantly different from control IgG treated mice (p=0.006). Mice co-implanted with NCI-H292 tumors and PBMCs dosed with 2.14H9OPT at 10 mg/kg, qw, ip result in a T/C of 54% that is not significantly different in comparison to treatment with human IgG (P=0.102).

CD3-Positive T Cell Infiltration

In experiments performed essentially as described in this assay, by IHC analysis, co-implantation of mice with the lung tumor line H292 and human PBMCs as a control arm results in a 10% increase of human CD3 T cells present in the tumor as measured on day 36 following implantation, while animals implanted only with H292 cells have a 3% increase of CD3 T cells. Treatment with PBMC and Antibody A (dosed at 10 mg/kg qw, i.p.) results in a 13% increase of human CD3 T cells; the statistical significance of the PBMC+Antibody A treated group compared to the PBMC+ IgG control group has a p-value of 0.021. Treatment with PBMCs and 2.14H9OPT (dosed at 10 mg/kg, qw, i.p.) does not increase the % human CD3 T cell infiltration as compared to the controls treated with IgG co-implanted with H292 cells and human PBMC (9% CD3 T cells for 2.14H9OPT vs. 10% CD3 T cells for control).

Established Human Tumor Xenograft Model in NSG Mice Humanized with PBMC

The efficacy of the antibodies of the present invention can be tested in the NCI-H827 human NSCLC xenograft model to assess the ability to delay or destroy established tumors in the model. On day 0, $1\times10^7$ H827 cells are implanted subcutaneously into the flank of NSG mice (7 weeks of age, female, 10 mice per group). With the human xenograft tumor established, the mice are infused (i.v.) with $5\times10^6$ human PBMCs on day 34. Starting on day 35, mice are dosed at 10 mg/kg by weekly (3 total doses) i.p. with either human IgG or the PD-L1 antibody. Animal well-being and behavior, including grooming and ambulation are monitored at least twice per week. Body weight and tumor volume are measured twice a week.

In experiments performed essentially as described in this assay, treatment with Antibody A significantly inhibits tumor growth in the humanized NSG mice, compared to treatment with human IgG (Table 2).

TABLE 2

| Tumor volume (mm³) in the NCI-H827 human NSCLC xenograft model | | | | | | | | |
|---|---|---|---|---|---|---|---|---|
| Treatment | Days | 21 | 28 | 30 | 34 | 36 | 40 | 43 | 47 |
| Hu IgG | Mean | 156 | 290 | 337 | 397 | 445 | 726 | 779 | 883 |
|  | SEM | 15 | 13 | 24 | 34 | 60 | 59 | 75 | 78 |
| Antibody A | Mean | 163 | 293 | 336 | 367 | 379 | 433 | 557 | 468 |
|  | SEM | 13 | 26 | 25 | 20 | 51 | 35 | 54 | 41 |
| Treatment | Days | 50 | 55 | 57 | 62 | 65 | 69 | 72 | 76 |
| Hu IgG | Mean | 959 | 1000 | 1241 | 1345 | 1530 | 1508 | 1854 | 2056 |
|  | SEM | 87 | 69 | 102 | 91 | 52 | 90 | 121 | 123 |
| Antibody A | Mean | 503 | 593 | 580 | 672 | 625 | 775 | 772 | 691 |
|  | SEM | 76 | 85 | 105 | 154 | 170 | 202 | 221 | 231 |

The efficacy of the antibodies of the present invention can also be tested by measuring the immune response to alloantigens in the NCI-H292 human NSCLC xenograft model.

On day 0, $2 \times 10^6$ H292 cells are implanted subcutaneously into the flank of NSG mice (7 weeks of age, female, 10 mice per group). After the tumor is established, the mice are infused (i.v.) with $10 \times 10^6$ human PBMCs on day 17. Starting on day 18, mice are dosed at 10 mg/kg by weekly ×3 (3 total doses) i.p.s with antibody. Animal well-being and behavior, including grooming and ambulation are monitored at least twice per week. Body weight and tumor volume are measured twice a week. On days 32-36, mice are sacrificed and blood is analyzed for peripheral T cell engraftment using TruCount™ tubes to evaluate the impact on peripheral engraftment of the human T-cell compartment, as well as the exhaustion phenotype of the T-cell subsets.

In experiments performed essentially as described in this assay on two mice per group, tumor-bearing mice treated with Antibody A display an altered CD4:CD8 ratio favoring the CD8 compartment compared to the human IgG treated group (Table 3; 63% of T cells were CD8 for Antibody A, compared to 47% for IgG control). The Antibody A treated group does not differ significantly from the IgG treated group in terms of absolute peripheral T-cell counts (CD4 count+CD8 count), but does display higher peripheral T cell counts than the 2.14H9OPT treated group ($43 \times 10^3$ cells/µl of blood for hIgG, $45 \times 10^3$ cells/µl of blood for Antibody A, and $10 \times 10^3$ cells/µl of blood for 2.14H9OPT).

When monitoring T cell activation, PD-1 levels on T cells may be looked at as a hallmark of exhausted T cells. A smaller number of PD-1+ T cells versus the control, suggests a greater T cell activation with the PD-L1 antibody. In this study with two mice per group, a decrease is seen in the PD-1 expression on T-cells in the Antibody A treated group (15% PD-1+) and the 2.14H9OPT treated group (32% PD-1+) compared to the IgG treated group (53% PD-1+).

TABLE 3

| Effect of Antibody A treatment on peripheral T cell engraftment in the H292 human NSCLC xenograft model | | | | |
|---|---|---|---|---|
| Treatment | Mouse | CD8 count | CD4 count | CD4/CD8 Ratio |
| 10M PBMCs + hIgG | #1 | 16801 | 19591 | 1.17 |
|  | #2 | 23832 | 26295 | 1.10 |
| 10M PBMCs + 2.14H9OPT | #1 | 9317 | 8611 | 0.52 |
|  | #2 | 1577 | 1419 | 0.67 |
| 10M PBMCs + Antibody A | #1 | 28879 | 15095 | 0.92 |
|  | #2 | 27450 | 18319 | 0.90 |

Mixed Lymphocyte Reaction

The function of blocking of PD-L1 signals by antibodies of the present invention may be evaluated by measuring the release of cytokines during T cell activation. The levels of certain cytokines, such as IFN-γ, are expected to increase if T cell activation is promoted by treatment with antibodies of the present invention.

CD14+ monocytes are isolated from fresh human PBMC obtained from a healthy donor (AllCells) with MACS beads (Miltennyi). Immature dendritic cells (DC) are generated by culturing these monocytes in 12 ml complete RPMI-1640 medium in the presence of 1000 IU/ml hGM-CSF and 500 IU/ml hIL-4 for 4 days. CD4+ T cells are purified from fresh human PBMC of a different healthy donor (AllCells) by negative selection (Milteny). The two types of cells are then mixed in individual wells of a 96-well plate with 100 µl complete AIM-V medium containing $1 \times 10^5$ CD4+ T cells and $4 \times 10^3$ immature DC per well (E:T=25:1). 100 µl complete AIM-V medium is added containing 2 nM human IgG1 or human PD-L1 antibody in 6 replicates. After incubation for 2 days at 37° C. at 5% $CO_2$, supernatants are harvested and measured for human IFN-γ with an ELISA kit (R&D Biosystems).

In experiments performed essentially as described in this assay, addition of Antibody A, S70, or 2.14H9OPT each enhance IFN-γ production by T lymphocytes in a dose-dependent manner. At the highest concentration tested (33.3 nM), Antibody A has an increase of 5.71 fold compared to 3.05 fold (S70), and 4.51 fold (2.14H9OPT).

TABLE 4

| IFN-γ secretion fold change vs. IgG control | | | | | | |
|---|---|---|---|---|---|---|
| | Antibody Concentration (nM) | | | | | |
| | 0.01 | 0.05 | 0.27 | 1.3 | 6.7 | 33.3 |
| Antibody A | 1.25 | 1.95 | 2.68 | 4.13 | 4.11 | 5.71 |
| S70 | 1.03 | 1.40 | 1.90 | 2.27 | 2.82 | 3.05 |
| 2.14H9OPT | 1.26 | 2.27 | 2.96 | 4.55 | 3.24 | 4.51 |

Heavy Chain Dominance of Antibody

The structure of the Antibody A/hPD-L1 co-complex is solved for two separate crystals at 3.7 Å and 3.2 Å resolutions. When analyzed, each shows the HCDR3 region of Antibody A directly contacting hPD-L1 while the LCDR3 of Antibody A points away from the epitope. The CDRs of the light chain of Antibody A have no significant contacts with either of the hPD-L1 domains. Within a 6 Å cutoff, the paratope of Antibody A is comprised of eighteen heavy chain residues and only seven light chain residues. The PD-L1/PD-1 binding site amino acids have been reported in Lin et al. (2008) PNAS 105(8):3011-3016. The contacts made by the variable light chain of Antibody A on PD-L1 are not the amino acids involved in PD-L1/PD-1 interaction.

To confirm the heavy chain dominance of Antibody A seen in the crystal structure, the effect on binding is measured for antibodies where the heavy chain of Antibody A is paired with irrelevant light chains that replace the light chain of Antibody A. One pairing produced an antibody that bound comparably to PD-L1 by ELISA as Antibody A; this antibody contained a light chain where none of the Antibody A paratope amino acids are conserved in variable light chain CDRs. This result suggests that binding to PD-L1 by Antibody A is almost completely mediated by the heavy chain. The thermodynamic signature of Antibody A can be analyzed to assess if the heavy chain dominance positively affects binding of PD-L1.

De-Convoluting the Thermodynamic Signature of Antibody A

Superior association by an antibody to the target can be critical in developing a therapeutic antibody. An antibody that quickly recognizes and binds the target is a desirable characteristic for a therapeutic antibody. A dominance of binding by the heavy chain of the antibody can mean less conformational changes need to occur before binding.

To assess the possibility that the heavy chain dominance of Antibody A would yield desirable binding characteristics, the thermodynamic signature of PD-L1 blockade is de-convoluted. The thermodynamic studies are completed on Fabs of Antibody A, S70, and 2.14H9OPT.

The heavy and light chains of the Antibody A Fab, S70 Fab, and 2.14H9OPT Fab are cloned into the GS vector. Human 293-Freestyle cells (Invitrogen Corp., Carlsbad, Calif.) are cultivated and transfected with the GS vectors according to manufacturer's specifications in suspension shake flask cultures. Briefly, uncut plasmid DNA and 293 fectin are allowed to complex for 25 min HEK 293 cells are re-suspended in fresh medium (vortex to remove clumps) and subsequently combined with DNA/fectin complex before incubation at 37° C. The conditioned supernatant is harvested after 6 days and assayed for protein expression. The CaptureSelect™ IgG-CH1 Affinity Matrix (Thermo Fisher Scientific) kit is utilized to purify all Fabs from the HEK 293 expression supernatant.

Binding of the Fabs is performed by surface plasmon resonance (SPR). Amine coupling immobilization of human PD-L1 monomer as ligand on to sensor chip surface is performed at 25° C. Antibody A-Fab, S70-Fab and 2.14H9OPT-Fab are used each as an analyte, and injected over the human PDL-1 monomer immobilized sensor chip surface. All sample analytes are run in 3-fold series dilutions (starting concentrations of 3 nM for Antibody A and 9 nM for both S70 and 2.14H9OPT), 6 total dilutions with one duplicate at a middle concentration and a zero. The sample gradients are prepared in the running buffer HBS-EP (0.01M HEPES pH 7.4, 0.15M NaCl, 3 mM EDTA, 0.005% v/v surfactant P20). The binding experiments are repeated at four different temperatures: 20° C., 25° C., 37° C. and 42° C. Throughout the kinetics experiments, the flow rate is maintained at 30 µl/min and the association/contact time at 180 sec for all three Fabs. The dissociation times are 600 sec for S70-Fab and 420 sec for Antibody A-Fab and 2.14H9OPT-Fab. After dissociation, a 0.75 M NaCl, 25 mM NaOH solution regenerates the immobilized hPD-L1, and then the surface is stabilized for 30 sec with the running buffer. The regeneration contact times are 18 sec, 24 sec and 30 sec for 2.14H9OPT-Fab, S70-Fab and Antibody A-Fab consecutively. The binding kinetics are analyzed using the Biacore T200 Evaluation software (Version 3.0). Data is referenced to a blank flow cell, and the data is fitted to the 1:1 Langmuir binding model.

Van't Hoff plots for the interaction of hPD-L1 monomer with the Fabs of Antibody A, S70 and 2.14H9OPT are used. Steady-state, association, and dissociation are the three binding phases analyzed. MATLAB is utilized for the linear regression analysis. $R^2$ measure of goodness of fit of linear regression was ≥0.97 for all three Fabs in all three binding phases.

In experiments performed essentially as described in this assay, the LSMeans Student's T demonstrates that the slopes of all the linear plots are statistically different from each other except for the dissociation phase linear plots of the 2.14H9OPT-Fab and Antibody A-Fab.

For association, the Antibody A-Fab/hPD-L1 interaction has the most favorable association phase among all the complexes. $\Delta S_{on}$ is a measurement of association; the more negative the $\Delta S_{on}$ value, the more favorable the interaction. Antibody A has a $\Delta S_{on}$ value of −26.0 while S70 and 2.14H9OPT have $\Delta S_{on}$ values of −11.7 and −19.4, respectively. This data demonstrates a more favorable association interaction for Antibody A with PD-L1 than S70 and 2.14H9OPT under these conditions.

Binding Kinetics and Affinity

The kinetics and equilibrium dissociation constant ($K_D$) for human PD-L1 is determined for antibodies of the present invention using surface plasmon resonance (Biacore).

Immobilization of antibodies of the present invention as ligand on to sensor chip surface is performed at 25° C. Soluble human PD-L1-Fc fusion protein (and in some cases, cynomolgus monkey PD-L1-Fc fusion proteins) is injected as analyte at concentrations ranging from 0.0123 nM-9 nM. The analysis is performed at 37° C. The contact time for each sample is 180 sec at 30 µl/min. The dissociation time was 240-1500 seconds. The immobilized surface is regenerated for 18 seconds with 0.95 M NaCl/25 mM NaOH at 30 µl/min, and then stabilized for 30 seconds. Binding kinetics are analyzed using the Biacore T200 Evaluation software (Version 3.0). Data are referenced to a blank flow cell, and the data are fit to a 1:1 binding model.

In experiments performed essentially as described in this assay, Antibody A binds to human PD-L1 with a $K_D$ of 82 pM.

TABLE 5

Binding by SPR of Antibody A

| Binding to Antibody A | Kon (1/Ms) | Koff (1/s) | $K_D$ (pM) |
|---|---|---|---|
| Human PD-L1 | 1.40E+06 | 1.14E−04 | 82 |
| Cyno PD-L1 | 1.51E+06 | 1.84E−04 | 122 |

ELISA Analysis: Antibody a Binds to Recombinant PD-L1

The ability for antibodies of the present invention to bind human PD-L1 can be measured with an ELISA assay. For the PD-L1 binding assay, a 96-well plate (Nunc) is coated with human PD-L1-Fc (R&D Systems) overnight at 4° C. Wells are blocked for 2 h with blocking buffer (PBS containing 5% nonfat dry milk). Wells are washed three times with PBS containing 0.1% Tween-20. Anti-PD-L1 antibody or control IgG (100 ul) is then added and incubated at room temperature for 1 h. After washing, the plate is incubated with 100 µl of goat anti-human IgG F(ab')2-HRP conjugate (Jackson Immuno Research) at room temperature for 1 h. The plates are washed and then incubated with 100 µl of 3,3', 5,5'-tetra-methylbenzidine. The absorbance at 450 nm is read on a microplate reader. The half maximal effective concentration (EC50) is calculated using GraphPad Prism 6 software.

In experiments performed essentially as described in this assay, Antibody A binds to human PD-L1 with an EC50 of 0.11 nM. Antibody A retains its binding activities after 4 weeks under all three temperature conditions, 4° C., 25° C. and 40° C. Antibody A showed a similar binding activity to PD-L1 as S70 and 2.14H9OPT.

Flow Cytometric Analysis: Antibody A Binds to Cell Surface PD-L1

The ability for antibodies of the present invention to bind to cell surface expressed human PD-L1 can be measured with a flow cytometric assay. MDA-MB 231 cells (PD-L1-positive human breast adenocarcinoma cell line) are added to a 96 well U-bottom plate at $1.5 \times 10^5$ cells per well in 200 µl staining buffer and incubated at 4° C. for 30 min Plate are centrifuged at 1200 rpm for 5 min and supernatant removed. 100 µl of antibody-biotin (serially diluted by 1:4 starting from 10 ug/ml) is added. A total of 6 serial dilutions are evaluated. After incubation at 4° C. for 30 min, cells are washed twice with DPBS. 100 µl of detection buffer containing 5 µl streptavidin-PE is added. After incubation at 4° C. for 30 more min, plate is centrifuged and washed twice with DPBS. Cells are re-suspended in 200 µl DPBS for FACS analysis.

In experiments performed essentially as described in this assay, Antibody A binds to cell surface PD-L1 on MDA-MB231 cells in a dose dependent manner with an EC50 of 0.14 nM.

ELISA Analysis: Antibody A Blocks the Interaction of PD-L1 with PD-1

The ability for antibodies of the present invention to block PD-L1 binding to PD-1 can be measured in an ELISA assay. For the receptor-ligand blocking assay, varying amounts (of anti-PD-L1 antibody or control IgG are mixed with a fixed amount of biotinylated PD-L1-Fc fusion protein (100 ng/well) and incubated at room temperature for 1 h. The mixture is transferred to 96-well plates pre-coated with PD-1-Fc (1 µg/ml) and then incubated at room temperature for an additional 1 h. After washing, streptavidin HRP conjugate is added, and the absorbance at 450 nm is read. IC50 represents the antibody concentration required for 50% inhibition of PD-L1 binding to PD-1.

In experiments performed essentially as described in this assay, Antibody A blocks the interaction of PD-L1 with PD-1 with an IC50 of 0.95 nM. Antibody A retains its blocking activities after 4 weeks under all three temperature conditions, 4° C., 25° C. and 40° C. Antibody A demonstrates a similar ability to block PD-L1 interaction with PD-1 as S70 and 2.14H9OPT.

ELISA Analysis: Antibody A Blocks the Interaction of PD-L1 with B7-1

Human PD-L1 also binds to B7-1. The ability for antibodies of the present invention to block PD-L1 binding to B7-1 can be measured in an ELISA assay. The procedure for PD-L1/B7-1 blocking assay is similar to the PD-L1/PD-1 blocking assay, except that the plates are coated with 1 µg/ml B7-1-Fc (R&D Systems). The antibody concentration required for 50% inhibition of PD-L1 binding to PD-1 (IC50) is calculated using GraphPad prism 6 software.

In experiments performed essentially as described in this assay, Antibody A blocks the interaction of PD-L1 with B7-1 with an IC50 of 2.4 nM. Antibody A shows a similar ability to block the PD-L1 interaction with the B7-1 receptor as S70 and 2.14H9OPT.

Amino Acid and Nucleotide Sequences (human PD-L1)
SEQ ID NO: 1
MRIFAVFIFMTYWHLLNAFTVTVPKDLYVVEYGSNMTIECKFPVEKQLDL
AALIVYWEMEDKNIIQFVHGEEDLKVQHSSYRQRARLLKDQLSLGNAALQ
ITDVKLQDAGVYRCMISYGGADYKRITVKVNAPYNKINQRILVVDPVTSE
HELTCQAEGYPKAEVIWTSSDHQVLSGKTTTTNSKREEKLFNVTSTLRIN
TTTNEIFYCTFRRLDPEENHTAELVIPELPLAHPPNERTHLVILGAILLC
LGVALTFIFRLRKGRMMDVKKCGIQDTNSKKQSDTHLEET (HCDR1 of Antibody A)
SEQ ID NO: 2
KASGGTFSSYAIS (HCDR2 of Antibody A)
SEQ ID NO: 3
GIIPIFGTANYAQKFQG (HCDR3 of Antibody A)
SEQ ID NO: 4
ARSPDYSPYYYYGMDV (LCDR1 of Antibody A)
SEQ ID NO: 5
SGSSSNIGSNTVN (LCDR2 of Antibody A)
SEQ ID NO: 6
YGNSNRPS (LCDR3 of Antibody A)
SEQ ID NO: 7
QSYDSSLSGSV (HCVR of Antibody A)
SEQ ID NO: 8
QVQLVQSGAEVKKPGSSVKVSCKASGGTFSSYAISWVRQAPGQGLEWMGG
IIPIFGTANYAQKFQGRVTITADKSTSTAYMELSSLRSEDTAVYYCARSP
DYSPYYYYGMDVWGQGTTVTVSS (LCVR of Antibody A)
SEQ ID NO: 9
QSVLTQPPSASGTPGQRVTISCSGSSSNIGSNTVNWYQQLPGTAPKLLIY
GNSNRPSGVPDRFSGSKSGTSASLAISGLQSEDEADYYCQSYDSSLSGSV
FGGGIKLTVLG (HC of Antibody A)
SEQ ID NO: 10
QVQLVQSGAEVKKPGSSVKVSCKASGGTFSSYAISWVRQAPGQGLEWMGG
IIPIFGTANYAQKFQGRVTITADKSTSTAYMELSSLRSEDTAVYYCARSP
DYSPYYYYGMDVWGQGTTVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKRVEPKSCDKTHTCPPCPAPEAEGAPSVFLFP
PKPKDTLMISRTPEVTCVVVDVSHEDPEVKFNWYVDGVEVHNAKTKPREE
QYNSTYRVVSVLTVLHQDWLNGKEYKCKVSNKALPSSIEKTISKAKGQPR
EPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLS
PGK (LC of Antibody A)
SEQ ID NO: 11
QSVLTQPPSASGTPGQRVTISCSGSSSNIGSNTVNWYQQLPGTAPKLLIY
GNSNRPSGVPDRFSGSKSGTSASLAISGLQSEDEADYYCQSYDSSLSGSV -continued

FGGGIKLTVLGQPKAAPSVTLFPPSSEELQANKATLVCLISDFYPGAVTV

AWKADSSPVKAGVETTTPSKQSNNKYAASSYLSLTPEQWKSHRSYSCQVT

HEGSTVEKTVAPAECS (DNA of HC of Antibody A)

SEQ ID NO: 12

CAGGTCCAGCTGGTCCAGTCAGGGGCCGAGGTCAAAAAGCCAGGGTCATC

TGTCAAAGTGTCTTGTAAGGCATCCGGGGCACATTTTCCAGCTACGCTA

TCTCCTGGGTGAGACAGGCACCAGGGCAGGGTCTGGAGTGGATGGGCGGA

ATCATTCCCATCTTCGGGACCGCCAACTACGCTCAGAAGTTTCAGGGAAG

GGTCACTATTACCGCCGACAAAAGCACATCTACTGCTTATATGGAGCTGT

CTAGTCTGAGGTCTGAAGATACCGCAGTGTACTATTGCGCCCGGAGTCCC

GACTATAGCCCTTACTATTACTATGGCATGGATGTCTGGGGCCAGGGAAC

CACAGTGACAGTCTCATCCGCTAGCACCAAGGGCCCATCGGTCTTCCCCC

TGGCACCCTCCTCCAAGAGCACCTCTGGGGGCACAGCGGCCCTGGGCTGC

CTGGTCAAGGACTACTTCCCCGAACCGGTGACGGTGTCGTGGAACTCAGG

CGCCCTGACCAGCGGCGTGCACACCTTCCCGGCTGTCCTACAGTCCTCAG

GACTCTACTCCCTCAGCAGCGTGGTGACCGTGCCCTCCAGCAGCTTGGGC

ACCCAGACCTACATCTGCAACGTGAATCACAAGCCCAGCAACACCAAGGT

GGACAAGAGAGTTGAGCCCAAATCTTGTGACAAAACTCACACATGCCCAC

CGTGCCCAGCACCTGAAGCCGAGGGGCACCGTCAGTCTTCCTCTTCCCC

CCAAAACCCAAGGACACCCTCATGATCTCCCGGACCCCTGAGGTCACATG

CGTGGTGGTGGACGTGAGCCACGAAGACCCTGAGGTCAAGTTCAACTGGT

ATGTGGACGGCGTGGAGGTGCATAATGCCAAGACAAAGCCGCGGGAGGAG

CAGTACAACAGCACGTACCGTGTGGTCAGCGTCCTCACCGTCCTGCACCA

AGACTGGCTGAATGGCAAGGAGTACAAGTGCAAGGTCTCCAACAAAGCCC

TCCCATCCTCCATCGAGAAAACCATCTCCAAAGCCAAAGGGCAGCCCCGA

GAACCACAGGTGTACACCCTGCCCCCATCCCGGGAGGAGATGACCAAGAA

CCAAGTCAGCCTGACCTGCCTGGTCAAAGGCTTCTATCCCAGCGACATCG

CCGTGGAGTGGGAGAGCAATGGGCAGCCGGAGAACAACTACAAGACCACG

CCTCCCGTGCTGGACTCCGACGGCTCCTTCTTCCTCTATTCCAAGCTCAC

CGTGGACAAGAGCAGGTGGCAGCAGGGGAACGTCTTCTCATGCTCCGTGA

TGCATGAGGCTCTGCACAACCACTACACGCAGAAGAGCCTCTCCCTGTCT

CCGGGCAAA (DNA of LC of Antibody A)

SEQ ID NO: 13

CAGTCCGTCCTGACACAGCCACCCTCAGCCTCTGGCACCCCTGGGCAGCG

AGTGACAATCTCTTGTTCTGGGAGTTCCTCAAATATTGGTAGTAACACCG

TGAATTGGTACCAGCAGCTGCCCGGCACAGCACCTAAGCTGCTGATCTAT

GGAAACTCAAATAGGCCATCCGGAGTCCCCGACCGGTTCTCTGGTAGTAA

ATCAGGCACTTCCGCCAGCCTGGCTATTAGCGGGCTGCAGTCTGAGGACG

AAGCCGATTACTATTGCCAGTCTTACGATTCCAGCCTGTCTGGAAGTGTG

TTTGGCGGAGGGATCAAGCTGACCGTCCTGGGCCAGCCTAAGGCTGCCCC

CTCGGTCACTCTGTTCCCGCCCTCCTCTGAGGAGCTTCAAGCCAACAAGG

CCACACTGGTGTGTCTCATAAGTGACTTCTACCCGGGAGCCGTGACAGTG

GCCTGGAAGGCAGATAGCAGCCCCGTCAAGGCGGGAGTGGAGACCACCAC

ACCCTCCAAACAAAGCAACAACAAGTACGCGGCCAGCAGCTACCTGAGCC

TGACGCCTGAGCAGTGGAAGTCCCACAGAAGCTACAGCTGCCAGGTCACG

CATGAAGGGAGCACCGTGGAGAAGACAGTGGCCCCTGCAGAATGCTCT

---

We claim:

1. An antibody that binds human PD-L1 (SEQ ID NO: 1), comprising a light chain (LC) and a heavy chain (HC), wherein the light chain comprises a light chain variable region (LCVR) and the heavy chain comprises a heavy chain variable region (HCVR), and wherein the LCVR comprises light chain complementarity determining regions LCDR1, LCDR2, and LCDR3 consisting of the amino acid sequences SGSSSNIGSNTVN (SEQ ID NO: 5), YGNSNRPS (SEQ ID NO: 6), and QSYDSSLSGSV (SEQ ID NO: 7), respectively, and wherein the HCVR comprises heavy chain complementarity determining regions HCDR1, HCDR2, and HCDR3 consisting of the amino acid sequences KASGGTFSSYAIS (SEQ ID NO: 2), GIIPIFGTANYAQKFQG (SEQ ID NO: 3), and ARSPDYSPYYYYGMDV (SEQ ID NO: 4), respectively.

2. The antibody of claim 1, wherein the LCVR has the amino acid sequence given in SEQ ID NO: 9, and the HCVR has the amino acid sequence given in SEQ ID NO: 8.

3. The antibody of claim 2, wherein the LC has the amino acid sequence given in SEQ ID NO: 11, and the HC has the amino acid sequence given in SEQ ID NO: 10.

4. The antibody of claim 3, comprising two light chains and two heavy chains, wherein each light chain has the amino acid sequence given in SEQ ID NO: 11, and each heavy chain has the amino acid sequence given in SEQ ID NO: 10.

5. The antibody of claim 4, wherein one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain.

6. The antibody of claim 5, wherein the antibody is glycosylated.

7. A mammalian cell comprising a DNA molecule comprising a polynucleotide sequence encoding a polypeptide having an amino acid sequence of SEQ ID NO: 11 and a polynucleotide sequence encoding a polypeptide having an amino acid sequence of SEQ ID NO: 10, wherein the cell is capable of expressing an antibody that binds human PD-L1 (SEQ ID NO: 1) comprising a light chain having an amino acid sequence of SEQ ID NO: 11 and a heavy chain having an amino acid sequence of SEQ ID NO: 10.

8. A process for producing an antibody that binds human PD-L1 (SEQ ID NO: 1) comprising a light chain having an amino acid sequence of SEQ ID NO: 11 and a heavy chain having an amino acid sequence of SEQ ID NO: 10, comprising cultivating the mammalian cell of claim 7 under conditions such that the antibody is expressed, and recovering the expressed antibody.

9. An antibody that binds human PD-L1 (SEQ ID NO: 1) produced by the process of claim 8.

10. A pharmaceutical composition, comprising the antibody of claim 1, and an acceptable carrier, diluent, or excipient.

11. A method of treating cancer, comprising administering to a patient in need thereof, an effective amount of the antibody of claim 1.

12. The method of claim 11, wherein the cancer is melanoma, lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or hepatocellular carcinoma.

13. The method of claim 12, further comprising administering simultaneous, separate, or sequential combination of one or more anti-tumor agents.

* * * * *